United States Patent [19]
Chow

[11] Patent Number: 5,496,473
[45] Date of Patent: Mar. 5, 1996

[54] APPARATUS FOR PROCESSING BIOPOLYMER-CONTAINING COLUMNS

[75] Inventor: Flora Chow, Bowie, Md.

[73] Assignee: Barrskogen, Inc., Bowie, Md.

[21] Appl. No.: 313,221

[22] Filed: Sep. 30, 1994

Related U.S. Application Data

[63] Continuation-in-part of Ser. No. 860,092, Mar. 30, 1992, abandoned.

[51] Int. Cl.$^6$ ................................................. B01D 15/08
[52] U.S. Cl. ........................ 210/635; 210/656; 210/101; 210/198.2; 210/416.1; 422/70; 422/101; 422/104; 530/412; 536/25.3; 536/25.31; 536/25.4
[58] Field of Search .................................. 210/635, 656, 210/101, 198.2, 416.1; 422/70, 90, 100, 101, 104; 530/412, 413, 417; 536/25.3, 25.31, 25.4

[56] References Cited

U.S. PATENT DOCUMENTS

| | | | |
|---|---|---|---|
| 3,926,809 | 12/1975 | Jones | 210/198.2 |
| 4,043,906 | 8/1977 | Helmer | 210/198.2 |
| 4,079,009 | 3/1978 | Seiler | 210/198.2 |
| 4,102,782 | 7/1978 | Saito | 210/198.2 |
| 4,362,699 | 12/1982 | Verlander | 422/131 |
| 4,517,338 | 5/1985 | Urea | 525/54.11 |
| 4,642,220 | 2/1987 | Bjorkman | 422/101 |
| 5,336,412 | 8/1994 | Huse | 210/635 |
| 5,378,359 | 1/1995 | Huse | 210/198.2 |
| 5,378,360 | 1/1995 | Huse | 210/198.2 |

OTHER PUBLICATIONS

Fisher 88, published 1988 by Fisher Scientific, p. 902.

Primary Examiner—Ernest G. Therkorn
Attorney, Agent, or Firm—Philip M. Goldman

[57] ABSTRACT

An apparatus has been designed that is useful for the automated or semi-automated removal, recovery, deprotection, and/or purification of biopolymers such as oligodeoxyribonucleotides, oligoribonucleotides, oligosaccharides, and peptides from a solid support matrix that is contained in a reaction chamber in the shape of a column.

13 Claims, 5 Drawing Sheets

APPARATUS FOR PROCESSING BIOPOLYMER-CONTAINING COLUMNS

This application is a 35 USC 371 of PCT/US93/03123, filed Mar. 29, 1993, which, in turn, is a continuation-in-part of U.S. Ser. No. 07/860,092, filed Mar. 30, 1992, now abandoned.

TECHNICAL FIELD

The present invention relates to an apparatus and process useful for the removal, recovery, deprotection, and/or purification of biopolymers attached to a solid matrix that is contained within a reaction chamber commonly shaped as a column.

BACKGROUND OF THE INVENTION

There are different practices in the operational procedures for use in the removal, recovery, deprotection and/or purification of biopolymers from a solid support. For example, when the biopolymer is newly synthesized DNA, the removal of DNA from the solid support, after completion of its synthesis, is accomplished by cleaving the chemical-bond that anchors the DNA polymer to the solid polymer matrix. In most applications, the chemical bond is an ester bond between a carboxylic acid and an alcohol (the 3'-hydroxyl group on the deoxyribose moiety of the sugar), which can be cleaved by hydrolysis using, for example, concentrated ammonia. The cleavage reaction is generally 80 to 100% complete within 1 hour at room temperature.

When the cleavage reaction (for the removal of the DNA) is done on DNA synthesizers that are equipped with an automatic cleavage feature (e.g., such as models presently available from Applied Biosystems or Milligen-Biosearch), the reaction is accomplished by pulsating concentrated ammonia through the synthesis column for about 1 hour, using an inert gas as propellant. The reaction time for the removal can be programmed into the machines, but is usually between 1 and 2 hours with a total aqueous ammonia consumption of 0.5 to 1.5 mL. The ammonia solution containing the recovered DNA polymer is collected in a vial attached to the machine. (During the cleavage operation the machines cannot be used for any other synthesis operations.) The recovered DNA polymer is next deprotected, purified and isolated, either in other instruments or by manual techniques.

Most DNA synthesizers are not equipped with the automatic cleavage feature for the DNA synthesis columns, and the cleavage reaction is instead done manually by laboratory personnel. DNA synthesizers without this feature are the most common, since they cost substantially less. The introduction of ammonia into the DNA synthesis columns can be done by many different manual procedures. The solid support in the column can be transferred to a vial containing aqueous ammonia, the vial sealed and allowed to stand at room temperature for about 1 hour; the vial can be heated to speed up the cleavage. The DNA is recovered in the supernatant, which is then separated from the solid support. The supernatant then undergoes further deprotection and purification procedures. This procedure for removing DNA from the support was commonly used several years ago when DNA laboratories packed their own DNA synthesis columns. Today most laboratories buy columns from chemical supply houses.

Nowadays, a modification of the above procedure is often used. Typically the column is removed from the synthesizer and a syringe is filled with aqueous ammonia (1 to 3 mL) and attached to the column. An empty syringe is fitted to the other end of the column to receive the ammonia that has passed through the column. From this point, the procedure may follow one of two methods. One method is to flush the entire contents of the feeding syringe through the column into the receiving syringe over the course of 10 to 30 seconds, and then allow the syringe unit to stand for 5 to 10 minutes. This is followed by a flush through the column in the other direction (the receiving syringe is now being used as feeding syringe, and the first feeding syringe now acts as the receiving syringe). This flushing back and forth should be done for at least 1 hour to achieve a nearly complete DNA removal from the DNA synthesis column.

A second method is to mimic the cleavage procedures used by the DNA machines. The contents of the feeding syringe (1 to 3 mL) are slowly pulsated through the column and collected in the receiving syringe. Since it is not possible to feed a very small amount of ammonia through the column continuously for 1 hour at a volume of 1 to 3 mL, a small amount (0.1 to 0.2 mL) is fed into the column, and the column is allowed to stand for 5 to 10 minutes before another addition of the same amount of ammonia. This procedure is repeated several times during the course of about 1 hour. Thus, about 0.1 to 0.2 mL of ammonia should be added to the column every 5 to 10 minutes for about 1 hour to achieve a nearly complete removal of the DNA attached to the DNA synthesis column. The DNA is recovered in the aqueous ammonia, collected in the receiving syringe. The DNA is ready for further deprotection and purification.

The DNA that has been removed and recovered from the DNA synthesis column contains a lipophilic protecting group at the 5'-end of the sequence (dimethoxytrityl group, also called the "DMT-group"), unless that group has been removed on the DNA synthesizer. Removal of the DMT-group is an option on the DNA synthesizer. Depending on the research and purification needs, the researcher may, or may not, choose this option. After the DNA, with or without the DMT-group, has been removed from the DNA synthesis column, it is deprotected at the bases and at the phosphorus using heated ammonia. The DMT-group is stable in ammonia and is not removed in the deprotection protocol when the DNA containing that group (i.e., "DMT-DNA") is heated at 55° C. for 5 to 24 hours to remove remaining protecting groups on the DNA polymer.

The DMT-DNA can be purified using affinity chromatography or reversed phase chromatography. High performance liquid chromatography ("HPLC") is often used for the purification, eluting the DMT-DNA on a reversed phase HPLC column using acetonitrile/triethylammonium acetate as eluent. The DMT-group is then removed under acidic conditions (80% aqueous acetic acid at room temperature for 15 to 60 minutes) and the fully deprotected DNA can be used after concentration of the eluent.

Recently, an alternative to the expensive HPLC isolation of DNA was introduced; the procedure is called cartridge purification. It is based on the same principle as reversed phase HPLC, in that the purification cartridge contains a lipophilic solid matrix to retain the DMT-DNA in the cartridge during the purification, while organic material from the deprotection procedure and non-DMT-DNA is washed off the cartridge. The cartridge purification does not have the resolution power of HPLC purification, but is sufficient for most DNA applications. There is one major difference between using HPLC purification versus cartridge purification; instead of removing the DMT-DNA from the cartridge, as is usually done on HPLC purification, the DMT-group is removed from the DMT-DNA with acid while the DMT-DNA is still on the cartridge. Then the fully deprotected DNA is then eluted off the cartridge with acetonitrile (20%) in water. The DNA is ready to be used after the solvent is evaporated.

The DNA cartridge purification is typically done by feeding reagents and solvents into the cartridge, shaped as a column, in a prescribed order, using a syringe. The cartridge is first washed with acetonitrile, then with triethylammonium acetate (1 to 2 M). The deprotected DMT-DNA is slowly applied to the cartridge in concentrated or diluted ammonia; it is generally recommended that the solution be passed through the cartridge at least 2 times. The cartridge is then washed with diluted ammonia to remove salts and non-DMT-DNA. The cartridge is next washed with water to remove the ammonia. The DMT-group is then removed with 1 to 2% trifluoroacetic acid by feeding the solution through the cartridge. The cartridge is then washed with water and the fully deprotected DNA is removed from the cartridge by aqueous acetonitrile. The DNA sample is concentrated and the DNA can be used.

This multi-step procedure is typically performed manually for each DNA sample. Because of the manipulations, this procedure involves a substantial amount of work and time. The solvents and reagents are fed by a syringe through the cartridge. The syringe has to be reloaded for each step. After several purifications, it can become a physical burden for the researcher to continue using the same thumb to push the syringe plunger in order to deliver the chemicals, or solvents, into the tightly packed cartridge. The cartridge purification takes approximately 15 to 20 minutes for each sample. In a laboratory that processes many samples, the time and the labor involved can be quite substantial.

SUMMARY OF THE INVENTION

Figure 1:
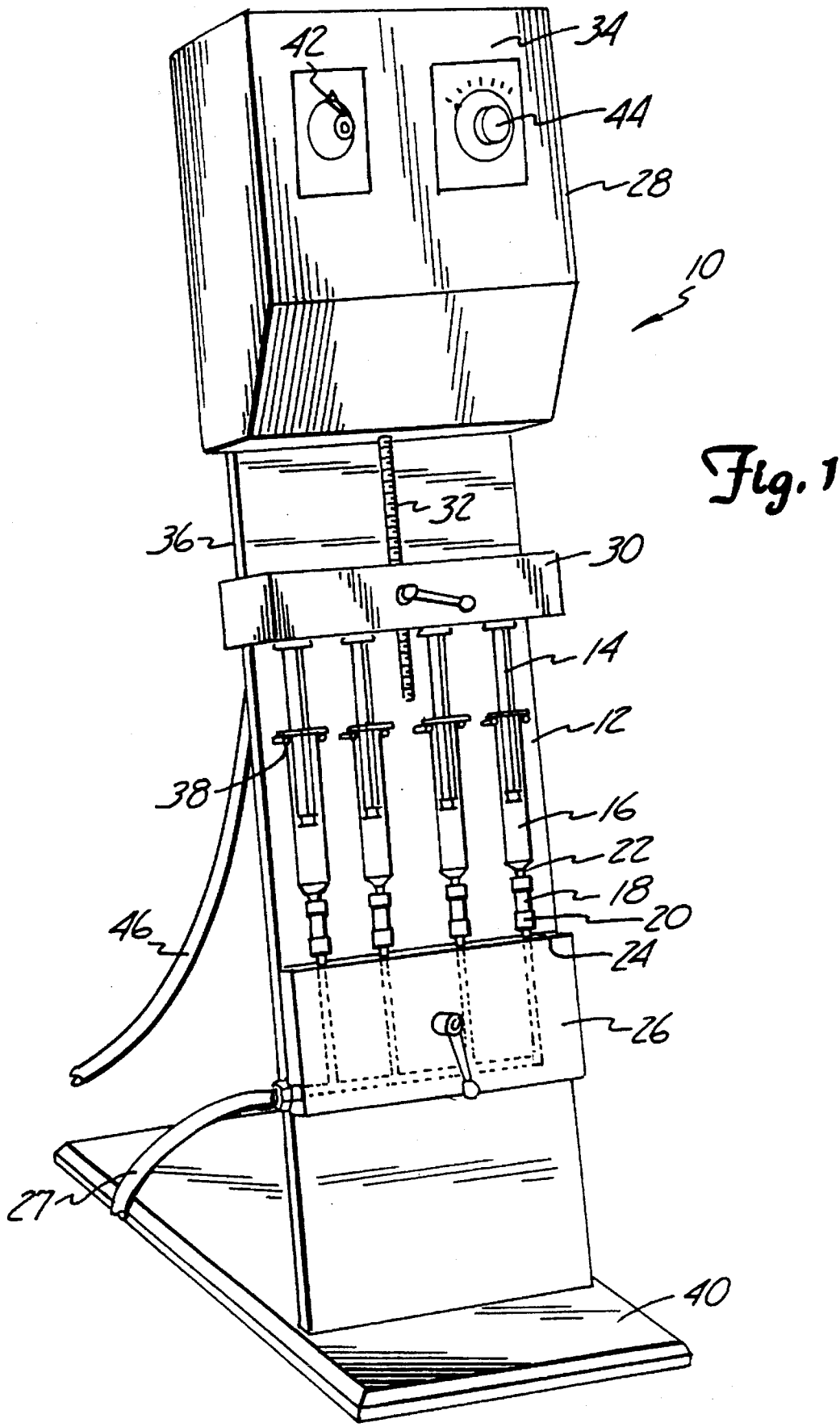
FIG. 1 is a perspective view of a preferred embodiment of the present invention for use as a cartridge purification apparatus.

The present invention provides an apparatus useful for performing automated or semi-automated operations in the course of the removal, recovery, deprotection, and/or purification of biopolymers attached to a solid matrix that is contained in a reaction chamber commonly shaped as a column or cartridge. The apparatus allows the delivery of liquids containing chemicals and/or solvents into one end of the column, and the collection (i.e., recovery) of liquids at the opposite end of the column, e.g., for the collection of product.

Once such a product has been recovered from, for example, a DNA synthesis column, it can continue to be processed by the use of the present apparatus, e.g., in the course of performing a deprotection protocol wherein remaining protecting groups are removed from the biopolymer. The deprotected biopolymer can also be further purified using a protocol for the purification of the biopolymer itself from the matrix.

In particular, the present invention provides an apparatus for the automated delivery of a liquid through a column that contains biopolymer attached to a solid matrix, the apparatus comprising, (a) a substantially cylindrical column, comprising a solid matrix, the column having, at opposite ends thereof, an inlet port and an outlet port, the inlet port being in fluid communication with the delivery means, (b) syringe-like liquid delivery means comprising a movable plunger within a cylindrical barrel, the delivery means being capable of receiving and holding the liquid and being in fluid communication with the inlet port of the column, and capable of delivering the liquid into the inlet port of the column upon depression of the plunger, (c) liquid receiving means in fluid communication with the outlet port of the column, (d) drive means capable of depressing the plunger in a controlled fashion, comprising;

(i) plunger engagement means for contacting, in order to depress, the plunger, (ii) linkage means capable of moving the plunger engagement means in response to the operation of a motor, and (iii) a motor capable of moving the engagement means at a controlled rate to depress the plunger, thereby delivering the liquid to the column, and (e) support means capable of retaining the drive means in operational alignment with the delivery means, and capable of releasably receiving and supporting the barrel, the column, and the receiving means in axial alignment with each other.

The present invention also provides a process for the removal, recovery, deprotection, and/or purification of biopolymers from a solid matrix contained within a column, the process comprising the steps of:

(a) attaching the column in an apparatus as described above, (b) sequentially delivering desired liquids useful for the removal, recovery, deprotection, and/or purification of the biopolymer through the column by the use of the apparatus, and (c) recovering desired fractions of the delivered liquids.

In one embodiment, the process of the present invention involves the use of ammonia for the cleavage and deprotection, or cleavage alone, of the synthesized DNA. In a particularly preferred embodiment, the process of the invention is a non-ammonia based one that involves the use of a base reagent for cleavage/deprotection, and either an acidic precipitating solvent reagent for precipitation/neutralization of DNA, or a non-acidic precipitating solvent reagent for the precipitation of DMT-DNA.

In another preferred embodiment, non-ammonia based reagents are provided for the rapid cleavage, deprotection and recovery of synthetic DNA, such reagents being particularly well suited for use on the apparatus of the present invention.

Such embodiments of the process of the present invention are facilitated by the automated nature of the present apparatus. The DNA producer or DNA user is able to automate the routine manual operations that follow solid phase synthesis, without sacrificing product quality. For instance, the total processing time for DNA can be reduced to on the order of one hour, thereby freeing up critical laboratory equipment for other purposes, and allowing the researcher to use the synthesized DNA the same day it is made.

DETAILED DESCRIPTION OF THE INVENTION

The present invention provides an apparatus for the removal, recovery, deprotection, and/or purification of biopolymers such as oligodeoxyribonucleotides, oligoribonucleotides, oligosaccharides, and peptides from a solid matrix contained in a chamber in the shape of a column.

A preferred embodiment of the present invention, i.e., wherein the apparatus is to be used for the removal of DNA from a column in which it has been synthesized, followed by the deprotection and recovery of the removed DNA, will be described with reference to the Drawing. It has been discovered that the removal of synthetic DNA from a solid support of the type typically used in its synthesis can be performed in an automated mode using an apparatus substantially as described in FIG. 5.

Figure 4:
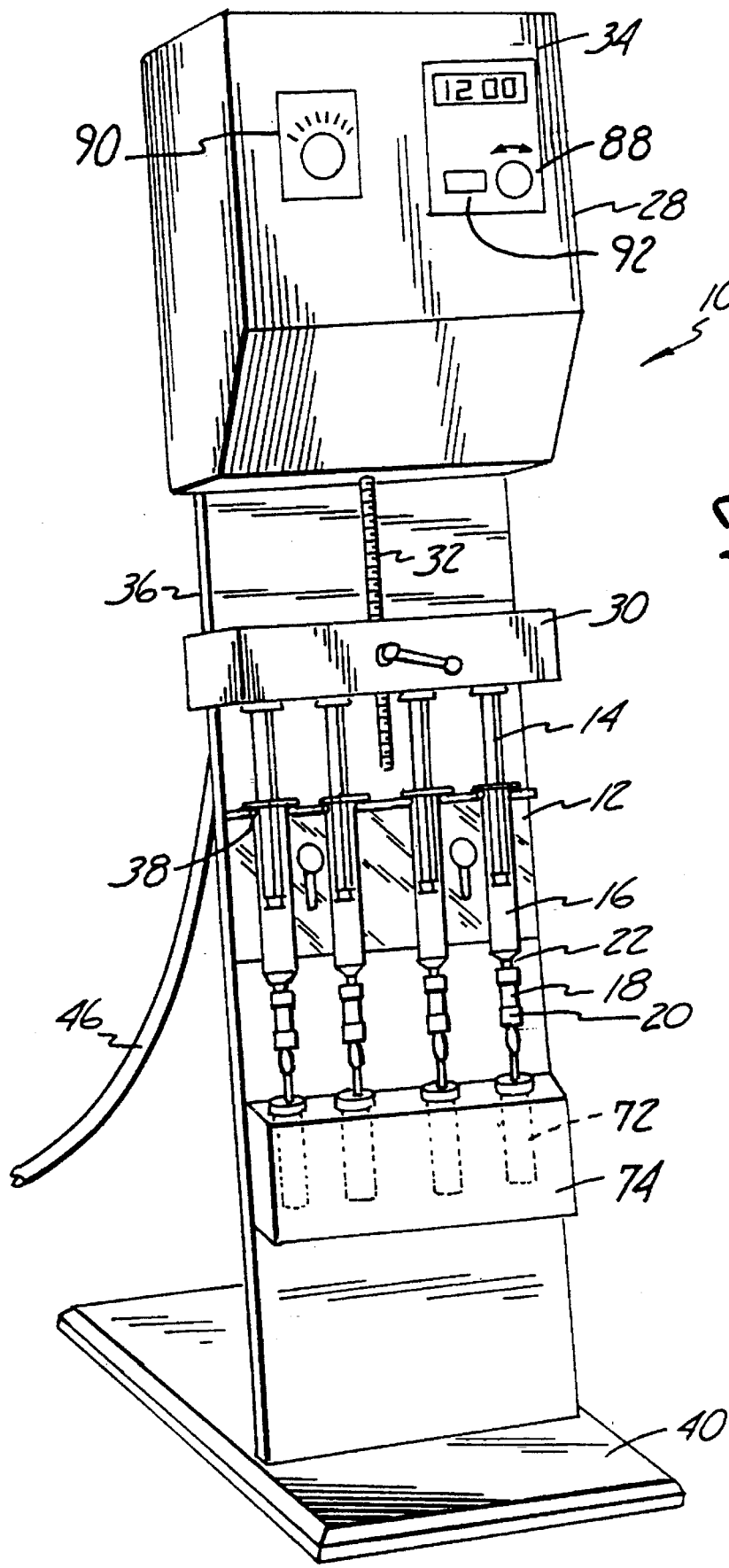
FIG. 4 is a perspective view of a preferred embodiment of the present invention for use as a cleavage and deprotection apparatus.
Figure 5:
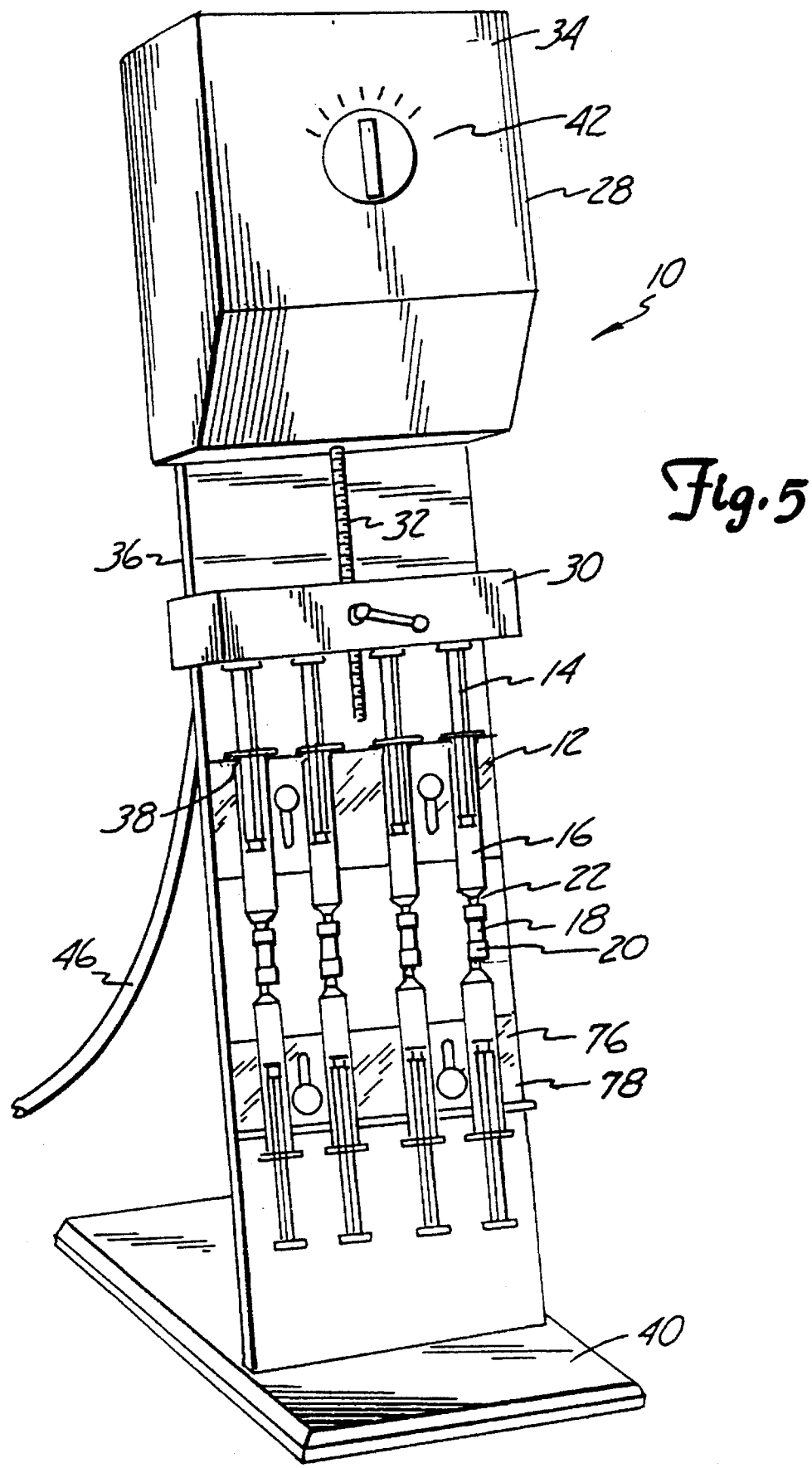
FIG. 5 is a perspective view of a preferred embodiment of the present invention for use as a cleavage apparatus.

FIG. 1 depicts an apparatus that is particularly well adapted for the purpose of cartridge purification. FIGS. 4 and 5, as will be described in greater detail below, depict apparatuses that are particularly well suited for the respective purposes of cleavage and deprotection, or cleavage alone.

In FIG. 1 there is seen an apparatus 10 comprising syringe-like delivery means 12 comprising a movable plunger 14 within a cylindrical barrel 16, delivery means 12 being capable of receiving and holding a liquid (not shown) and being capable of delivering the liquid into column 18 upon depression of plunger 14. For purposes of brevity, delivery means 12 will alternatively be referred to as simply a syringe, or the delivery syringe.

Column 18 is substantially cylindrical and preferably contains a biopolymer attached to solid matrix 20. By this it is meant that the biopolymer is retained by a support material, that is itself contained within the column, in such a manner that at least a desired portion of the biopolymer will be retained on the support material, and within the column, in the course of its intended use. When the apparatus is used for the purification of columns, the columns themselves will typically contain the solid matrix, but may not necessarily contain biopolymer itself.

The column has, at opposite ends thereof, an inlet port 22 and an outlet port 24, inlet port 22 being in fluid communication with delivery means 12. The term "fluid communication", as used herein, refers to a mating relationship in which liquid flows without substantial leakage or loss, e.g., in which the male delivery port of a syringe is matably seated with a female inlet port of a column. Column 18 is generally provided by the user of the apparatus, e.g., from a DNA synthesis machine and attached to the apparatus as described herein.

"Biopolymer", as referred to herein, can be of any desired type and size, e.g., nucleic acid, protein, lipoprotein, polysaccharide, lipopolysaccharide, and combinations thereof. Biopolymer can be "attached" by any means, or combination of means, suitable for its intended use, e.g., through chemical bond attachment, affinity attachment, ion exchange attachment, or through size exclusion attachment.

Columns can contain solid matrices in the form of, for instance, particles (such as solid, porous, or hollow beads), permeable or impermeable membranes, stable emulsified droplets, and solid support surfaces in any desired configuration.

Also seen in FIG. 1 is liquid receiving means 26, in fluid communication with outlet port 24 of column 18. The liquid receiving means suitable for use in the apparatus of the present invention depend, in large part, on the intended use of the apparatus. Such receiving means can, for instance be in the form of another syringe-like device, which can be used to hold and/or re-deliver the liquid to the column. Such syringe-like devices are shown in FIG. 5, where it can be seen that opposing syringes 76 are each retained in the outlet port of each cartridge by means of a syringe holder 78 similar in nature and use to the holder that retains the upper syringe set.

Alternatively the receiving means can be in the form of a vial or tube, for separately collecting any liquids delivered to the column. As seen in FIG. 4, for instance, the receiving means is in the form of a plurality of vials placed within heated block 74. Heated block 74 is provided in the form of a metal (e.g., aluminum) block of sufficient dimensions to allow a plurality of vials (e.g., 4 ml, 15×45 mm) to be inserted and retained, and there warmed to the desired temperature. The block is preferably heated by the use of a thin heating pad or element (not shown), such as is a placed between the block and the apparatus surface. A suitable heating element for such purposes would be the flexible silicone rubber fiberglass insulated heater, 2 inches by 6 inches in size, having a total wattage of 120 watts, and a watt density of 10 watts per square inch (Omega, no. SRFG-206-10). The heating pad is itself electrical, powered by an electric cord (not shown) leading through the support to the rear of the apparatus.

In yet another embodiment, the receiving means can be in the form of a liquid passageway, e.g., in order to direct the liquid from the column to a waste receptacle such as a beaker. As presently shown in FIG. 1, liquid receiving means 26 is depicted as a solid block of material, e.g., plastic or metal, having passageways (shown as dotted lines) drilled through to allow liquid to be collected from each column; combined in a channel running parallel to the base of the apparatus, and flow out a common outlet tube 27. In a preferred embodiment, each of the passageways is substantially parallel to each other, and approximately equally spaced; is substantially parallel to, and in axial alignment with, the respective column for which it will serve as receiving means; and is in liquid communication with the outlet port of its respective column, e.g., whether by allowing liquid to drip directly into the passageway, or through a tube connection, or by a matable syringe-like relationship. Each of the passageways, as shown, also terminates in a common channel which runs parallel to the base of the apparatus and at the bottom of the block, in this preferred embodiment, the channel running out the block and through a common outlet tube as waste. In an alternative embodiment, liquid from each of the passageways can be individually collected, or shunted, combined, and collected in any desired combination and manner.

The passageways are preferably each of a suitable dimension to allow a common laboratory tube, e.g., a 1.5 ml.

microcentrifuge tube such as those available under he trade names "Clickseal," or "Eppendoff," to be placed in each passageway and there held by virtue of the lip of the tube resting on the entrance to the passageway. Such tubes are desirable in order to individually collect liquids, in the event the liquid contains the desired eluted material.

In a preferred embodiment, an apparatus of the present invention will be provided having one configuration of receiving means and controls, with the option of obtaining one or more accessory kits, (e.g., containing alternative receiving means and associated hardware and instructions) that would allow the user to retro-fit the basic apparatus into any other desired configuration.

Figure 6:
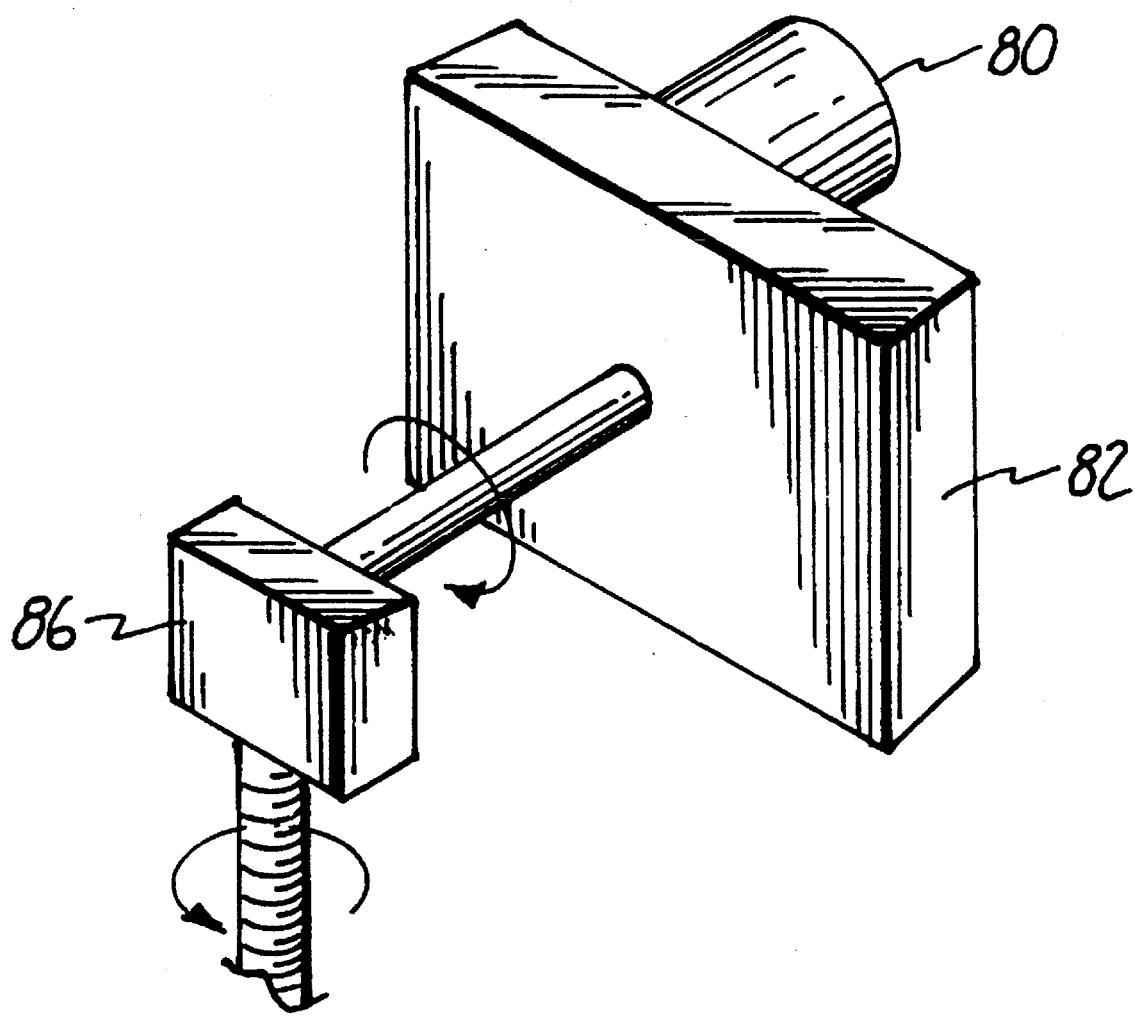
FIG. 6 is a schematic view of the drive means of a preferred apparatus.

FIG. 1 also depicts drive means 28 of a preferred apparatus, which is capable of depressing plunger 14 in a controlled fashion in order to deliver liquid from delivery means 12 into column 18. Drive means 28 is shown as comprising (a) block-like plunger engagement means 30, (ii) linkage means 32 capable of moving engagement means 30 in response to the operation of a motor, and (iii) motor, (not shown, but housed within the depicted cabinet 34) capable of moving engagement means 30 at a controlled rate to depress plunger 14, thereby delivering liquid to column 18. The linkage means and motor is shown in FIG. 6, wherein it can be seen that the operation of motor causes gear box 82 to rotate shaft 82, which in turn causes the rotation of threaded rod 32 by means of coupler 86.

In a particularly preferred embodiment, plunger engagement means 30 is in the form of a cross-bar, capable of contacting the plunger of a plurality of syringes simultaneously; linkage means 32 is in the form of a rotatable threaded rod; and motor (housed within cabinet 34) is an electric motor. The position of the cross-bar is adjustable along the length of the rod-like linkage means, and can be releasably retained in such position by any suitable means.

The preferred apparatus of FIG. 1 further comprises support means 36 capable of retaining drive means 28 in operational alignment with delivery means 12. By "operational alignment" is meant that the drive means is mechanically positioned in such a manner as to be able to depress the plunger upon operation of the motor. Support means 36 is also capable of releasably receiving and supporting barrel 16, column 18, and receiving means 26 in axial alignment with each other. By "releasably receiving and supporting" is meant that each is capable of being removed, e.g., in order to be re-filled with liquid, and attached or replaced, at will, on the support, and there retained in a suitable manner for the delivery of the liquid. By "axial alignment" is meant that barrel 16, and therefor plunger 14, of delivery means 12, are positioned to directly or indirectly (e.g., through a flexible tube), inject or deliver the contained liquid into inlet port 22 of the column, and that receiving means 26 are similarly positioned with respect to outlet port 24 of the column.

Figure 3:
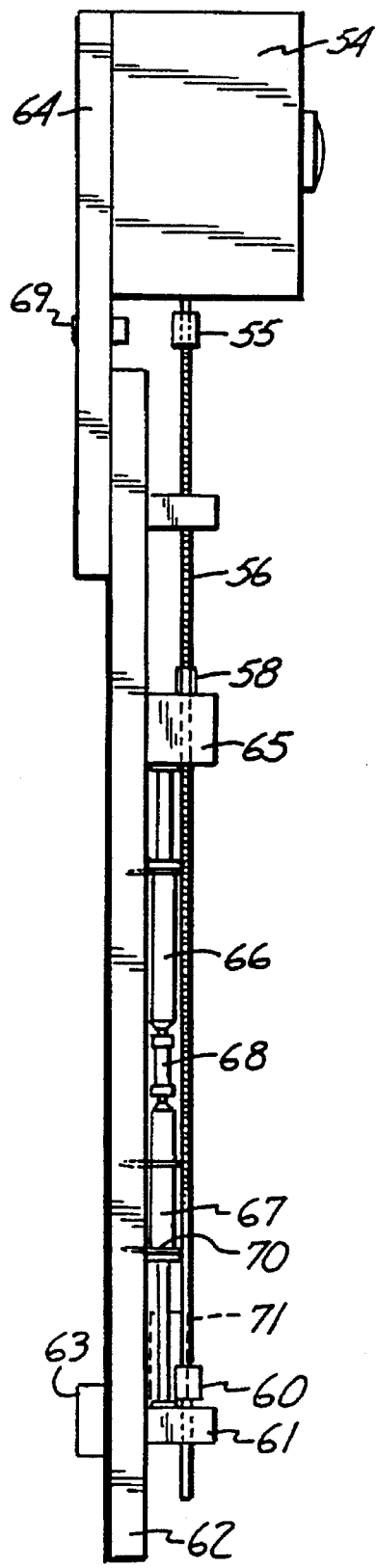
FIG. 3 is a side elevational view of the embodiment of FIG. 2.
Figure 2:
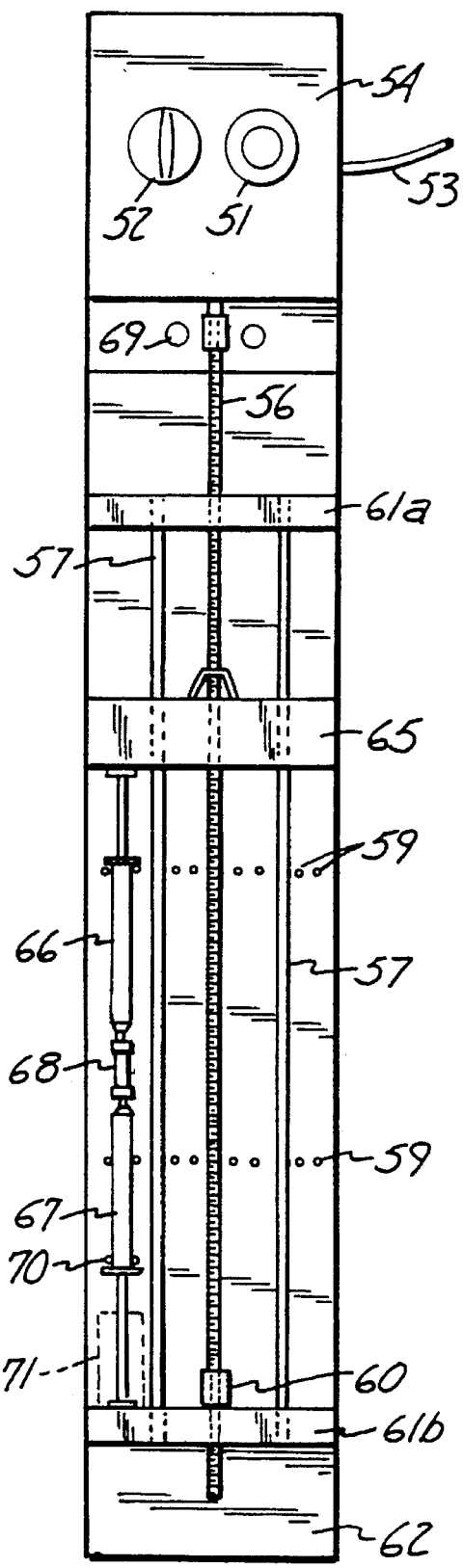
FIG. 2 is a top elevational view of a prototypic embodiment of the present invention.

Typically support means 36 includes a flat surface capable of holding the syringe, the column, and the receiving means in a planar, end-to-end relationship. As shown in FIG. 1, the support includes removable, adjustable pins 38, capable of being positioned in a manner sufficient to retain syringes of variety of sizes by allowing the upper flange of such syringes to rest on the pins and the cylindrical bodies to rest between adjacent pins. As shown in FIGS. 2 and 3, rather than individual adjustable pins, a unitary sheet is employed, having an upper lip that provides grooves for resting the upper flange of the syringe barrels. The portion of the flat syringe holder that lays upon the flat surface of the support means further includes a plurality of grooves, through which a positioning knob or knobs can be secured to the support, thereby securing the syringe holder in a desired position.

Support means 36 is itself typically capable of being held in an upright position, e.g., by base 40 in order that the syringe is retained above the column, the receiving means below, and the liquid flows generally downward. Also seen in FIG. 1 are timer 42 and motor speed control 44, described more fully below, as well as motor power cord 46. By analogy, the controls associated with the apparatus of FIG. 4 include a timer 88, a speed control 90, and a on/off switch 92 for the timer.

In a typical use of an apparatus such as that shown in FIG. 1, e.g., for the removal of synthetic DNA from the solid support used in its synthesis, the delivery syringe, containing concentrated aqueous ammonia (1 to 3 mL) is attached at one end of the column and an empty syringe is attached at the other end of the column. Liquid receiving means 26, presently depicted as a plastic block, can be removed entirely, enabling syringes to be inserted beneath each column. Optionally, the entire syringe-column-syringe assembly of the preferred embodiment can also be replaced with a similar assembly that allows for use of wide filtration discs (e.g., 1.25 inches in diameter).

The column and syringe assembly is placed on the apparatus, within the adjustable pins and thereby secured to the syringe-column-syringe assembly during the delivery of ammonia through the column. The delivery of liquids, e.g., containing chemicals or solvents, through the column is accomplished by activation of the motor, which in turn, moves the plunger engagement means in manner that depresses the plunger and delivers the liquid.

In a preferred embodiment, an apparatus of the present invention can simultaneously hold a plurality, e.g., 2, 3, or 4 syringes within parallel, approximately equally spaced paths at the same time, thus removing the DNA from up to four DNA synthesis columns at the same time. The continuous feeding of ammonia through the column is the most effective chemical procedure for the cleavage reaction. There are several competing reactions during the cleavage. (The most labile bond is the ester bond anchoring the DNA to the support; other susceptible bonds for hydrolysis are side chain protecting groups on the nucleoside bases and the cyanoethyl group on the phosphorous linking the nucleosides together.) During the cleavage, ammonia is thus consumed by several reactions, reducing its concentration in the column. The continuous feeding ensures maximum excess of ammonia, whereas the pulsation and flushing procedure results in less concentrated ammonia over time and with decreased reactivity as a result.

It is also disclosed that after the DNA has been removed and recovered in this apparatus, the DNA can also be deprotected on the apparatus at a specific temperature for a specific time chosen by the operator. Although the deprotection can be done separately on the apparatus, a more effective use is to prepare the apparatus for the deprotection step before the removal/recovery is started, thus providing an automation of the entire process. It is also disclosed that the apparatus can be used in a semi-automated mode, e.g., to purify DNA using reversed phase purification cartridges, preferably also at a rate of up to four cartridges at a time.

An apparatus such as that shown in FIG. 1 can be manufactured from any suitable material, e.g., wood, plastic, metal, or from any combination thereof. Preferably the linkage means is in the form of a rotatable, threaded metal rod. Preferably the motor used to drive the rotating threaded rod is an electric motor, which can have constant speed or variation of speed options ranging from 0.1 to 100 rpm for the disclosed applications. The use of speed controls extends the range to lower or higher rpm configurations as desired. The motor can be turned on or off by a switch or a timer that automatically stops the motor after a preset length of operational time, or it can be turned off by a limit switch, proximity switch, photoelectric switch or any combination thereof.

The size of the delivery syringe can be varied, depending on the scale of the operation, i.e., the quantity of biopolymer being processed; for large operations, a large capacity syringe, and for small operations, a small capacity syringe can be used. Small scale operations are generally run with about 0.1 to 1.0 mL solvent; intermediate scale, with 1 to 10 mL solvent; and large or preparative scale, with 10 to 250 mL solvent. The receiving means should have sufficient capacity to permit the desired amount of liquid to be collected, or be equipped with an emptying device to release fluid to a collection bottle. The apparatus can be placed in horizontal or vertical position depending on the characteristics of the columns used.

Generally a vertical or near vertical position of the apparatus or the columns are recommended for the generally loosely packed columns. A particularly preferred embodiment of the apparatus of the present invention can hold four syringe-column-syringe assemblies to be operated at the same time using syringes of up to 10-mL size. Modification of the syringe holders by increasing the spacing, size and integrity will allow for larger syringe-column/cartridge-syringe assemblies for the preparative and industrial scale applications. The laboratory applications using four assemblies at a time is not limited to that number since several apparatus can be used or the configuration of a single apparatus can be changed to hold even more assemblies, e.g., 8 assemblies, or even 12 assemblies, per apparatus.

The drive means can include an electric motor, a timer to control the time during which the motor will operate, and speed regulator for the control of the speed of the motor, and in turn control of the rate of delivery of the ammonia, i.e., the flow rate through the column. In use, the delivery syringe that will be feeding the chemical or solvent through the column is filled and attached to the column followed by the attachment of the empty receiving syringe. This assembly is put into the holder as mentioned above. The crossbar is snug fitted onto the plunger of the syringe, while avoiding moving either the delivery syringe or the plunger within the syringe. Any suitable means, e.g., a threaded bolt and wing nut, can be used to retain the crossbar at the desired position along the threaded rod and against the plungers.

Next, the apparatus controls are set. The desired flow rate is set by the motor speed control, e.g., 1 mL/hour or 2 mL/hour depending on preference of the operator. The desired length of the operation is set by the timer; for a removal operation, typically 1 hour is used for the removal of DNA synthesized on 0.2 to 1.0 micromolar scale. Lastly, the apparatus's main power is turned on. The 1 hour removal time is performed without necessitating the attention of a laboratory technician. At the end of the 1 hour, the ammonia solution has been collected in the second syringe (the receiving syringe). The ammonia solution, now containing the DNA that has been removed and recovered from the solid support, is transferred to a vial for further deprotection steps if that is preferred by the operator.

Optionally, the operator can continue processing the DNA by use of the automated deprotection features available with the present apparatus. If the recovered DNA is to be deprotected on the apparatus, the apparatus is preferably slightly modified (since the deprotection process requires periods of heating), before the removal/recovery routine by the operator for that purpose. After the syringe-column-syringe assembly is put on the apparatus, and the crossbar and wing nut are adjusted as described above, a cover e.g., of $\frac{1}{16}$" thick sheet metal aluminum with a dark surface for heat absorption is preferably placed over the entire unit. (The cover can also be made of plastic.) The cover can be of any suitable dimensions, e.g., 5½" wide, 24" long with sides of 24" long and 1½" high.

A thermocouple is preferably inserted into the unit through the holder and the crossbar and is positioned between and parallel to one of the syringe-column-syringe assemblies previously described. The thermocouple is connected by wire to a temperature controller which is set at 55° C. The controller is connected to a 250 watt heat lamp positioned about 6 inches from the cover surface with the light beam centered at about one-third of the distance from the bottom of the length of the apparatus. A timer starts the lamp, and the unit is heated up to 55° C., where it is shut of by the temperature controller, and turned on again when the temperature has fallen 2 degrees. The unit is maintained at a temperature of about 53°–55° C. The timer which starts the heat lamp is also set to turn off the heat lamp after 5 to 15 hours (The reaction requires at least 5 hours, but the reaction time may be extended for an overnight run without deleterious effects).

Preferably, the automated removal/recovery and deprotection made possible by the present apparatus would be used in the laboratory the end of the work day, i.e., when the DNA synthesis has usually been completed. The DNA synthesis column can be assembled for an overnight removal/recovery and deprotection of DNA on this apparatus. Following the 1-hour removal/recovery, the timer can start the heat lamp and the deprotection step started, with the deprotection time usually set to be completed before the next work day. The deprotected DNA can be used the next morning after the unit has cooled off.

The removal/recovery and deprotection process described above can be varied, as will become apparent to those skilled in the art. In order to speed up the removal of the DNA from the DNA synthesis column, means for controllably heating the columns are provided, e.g., a heating device (not shown) that can be turned on during the cleavage reaction to speed up the process. In order to prevent the built-up pressure and a too-fast delivery of the ammonia, a spring coil can be affixed to the plunger of the receiving syringe. Alternatively, a rubber band holding the plunger to the syringe barrel, or the roll pins, can serve the same purpose. It can be approximated that a 10-degree increase in reaction temperature corresponds to a two-fold increase in reaction speed. Thus, by setting the temperature control at 30° C, the removal time will be reduced to approximately 30 minutes compared with 1 hour at room temperature, and by setting the temperature control at 40° C., the time is reduced to about 15 minutes compared to 1 hour at room temperature. As a result, the present apparatus can a provide significant, e.g., at least a four-fold increase in the speed of removal of DNA from DNA synthesis columns as compared to commonly used procedures.

When the apparatus is to be used for the cartridge purification of DMT-DNA, the recommended protocol provided by the cartridge manufacturer for a manual operation is followed. Since these procedures use a syringe to feed solvents and reagents through the cartridge at a prescribed speed and volume, that same procedure is followed using the automated feeding and recovery procedure disclosed for the present apparatus. For each individual step, the delivery syringe is filled with appropriate reagent and placed on the cartridge, and an empty syringe (or waste block, or collection tube) is mounted at the other side of the cartridge. A plurality of collection tubes (not shown) can be inserted in order to individually collect the sample from each respective syringe. The assembly is placed on the apparatus, and the time and flow rate are set for the operation. The advantages of using this apparatus compared with the manual syringe method are substantial, e.g., at a configuration of 4-column assemblies, the cartridge purification can be done approximately 3 to 4 times faster than the presently used manual procedures. The work of pushing the syringe plunger is also alleviated and the reproducibility of the procedure is improved by the semi-automatic feature (i.e., the feeding of solvents and reagent are done automatically and the filling of the syringes and loading on the apparatus done by the operator manually, thus the terminology, semi-automated).

In another, and preferred embodiment, the apparatus of the present invention is used in a non-ammonia based two-step reagent process for the cleavage/deprotection and precipitation/neutralization of newly synthesized DNA. This process can lower the total processing time for newly synthesized DNA to on the order of one hour, without the need for additional equipment or a sacrifice in the quality of the resultant DNA. In such an embodiment, the first step is accomplished by the use of a basic reagent sufficient to raise the pH of the solution to between about pH 12 and about pH 14. The basic reagent can be provided in any suitable form, for instance, and is preferably one that provides a metal counter ion to the phosphate groups of the DNA. Sodium, potassium, calcium, and lithium salts are particularly useful. The reagent is preferably provided in an excess amount that is between about 5 and about 50 times the theoretical molar amount of DNA nucleotides present in the sample. In a preferred embodiment, the basic reagent is provided in the form of a 0.1 to 2 molar sodium hydroxide solution.

Following cleavage and deprotection, the DNA is treated with an acidic precipitating solvent (e.g., alcohol) reagent. Any non-interfering acid (i.e., substantially inert to DNA) can be used that is sufficient to neutralize the basic reagent, and obtain a pH of between about pH 6 and about pH 8. The precipitating solvent that is used is preferably miscible with water, but one in which DNA itself is either insoluble or of limited solubility. As a result, the DNA is able to precipitate from the mixture of precipitating solvent and water. Preferred precipitating solvents for this purpose included alcohols such as propanol and isopropanol, as well as tetrahydrofuran, and other suitable non-aqueous solvents.

In situations in which DMT-DNA is cleaved and deprotected, the resultant DMT-DNA can be precipitated by the use of precipitating solvent alone, that is, non-acidic solvent. Non-acidic precipitating solvent, such as 2-propanol, is preferred since the DMT-group is itself acid labile.

The use of the above-described basic/acidic precipitating solvent or basic/precipitating solvent steps with the apparatus of the present invention offers a rapid processing approach without detrimentally affecting the quality of the final product.

A preferred configuration of the apparatus, for use with loosely packed DNA columns, is in a vertical or near vertical position, i.e., with the delivery syringe-column-receiving syringe assembly from top to bottom, to ensure the most efficient removal of the DNA. Alternatively, the apparatus can be used in a horizontal position if the columns or cartridges are separately mounted in vertical position. In the latter configuration, a tubing connecting the feeding syringe to the column or cartridge may be preferred as well as a tubing connecting the other end of the column to the receiving syringe.

It is expected that most of the above operations on the apparatus can be controlled with a computer using parts that are compatible for such use. For instance, a geared stepping motor (such as model PF-55) in combination with a controller (models MC-400), as are available from Inland Motor Co. (Radford, Va.), can be designed for full or half stepping when interfaced with an "OP-1" or "OP-2" operator panel (or other suitable microprocessor), to provide a built-in display and push-button switching, thereby enabling e.g. the manual setting of program variables; automatic calibration features; customized features, and the like.

EXAMPLES

EXAMPLE 1

Prototype Apparatus

A prototype apparatus of the present invention was constructed in the following manner and will be described with reference to FIGS. 2 and 3. The apparatus included a wooden bottom plate 32 inches long, comprised of two mahogany planks, a long plank of approximately 24" long, ¾ high, and 5½" wide, and a shorter plank (64) that was 12" long, ¾" high, and 5½" wide. The two planks were nailed and glued together with a 4" overlap in order to provide a total length of 32". On the underside of the long plank, at the end away from the short plank, a mahogany piece ¾" long, 1½" high, 5½" wide nailed and glued 2" from the edge. (63)

Two wooden holders 5½"×¾"×1½" (61) and one cross bar 5½" ×1 ½"×1½" were made (65). A ⅜" hole for the threaded rod was drilled in the center of the 5½"×1½" surface area of each of the holders and crossbar. The center was 2¾" from the side and ¾" from the top. Symmetrically on both sides of the center hole were drilled ⅜" diameter holes 1⅜" from the center of the center hole. The two holders were mounted on the long plank (62), one over the location of the bottom mahogany piece (63) and one at the other end, both 2½" from the ends of the long plank, using glue and two nails for each holder.

Eight holes for the pins (59), for holding the syringe-column-syringe assembly, were drilled in a linear array 10" from the lower end of the long plank where it was connected to the small plank. At ¼" from the edge was drilled the first hole (3/32" in diameter) through the plank and a roll pin made of steel with a 3/32" diameter and 1" long was inserted into the hole leaving ½" above the surface. A second hole was drilled along the line with a space of ¾" to fit a plastic syringe 11/16" in diameter and a roll pin was inserted as above. A third hole was drilled ½" from the latter pin and the procedure was repeated in a linear array to give a total of 8 holes, where roll pins are inserted (59). The results are 4 spacings of ¾" width, for holding 4 syringes of 11/16" diameter. From that line of pins was then measured 6" for a new set of holes and roll pins, corresponding to the above measurements to give a symmetrical configuration.

Through the two outer holes of the holders and the crossbar was inserted ⅜" dowels (57) of about 24" long. The dowel was glued to the outer holes of the holders and cut flush with the outer surface of the holders. The crossbar could be moved along the long plank in a parallel mode to the holders. A 5/16" threaded rod (56) (18 threads/inch) was inserted through the centers of the holders and crossbar. The rod was introduced from the end of the long plank with the bottom mahogany piece. A shaft collar (60) (ID 5/16", OD 5/8", wide 3/8", Grainger 2X736) was loosely put on the rod when the leading end has passed through the hole of the first holder, the rod was continuously pushed through the center hole of the crossbar.

After the rod exited from the crossbar hole, a wing nut (58) was screwed onto the rod. The nut had ID of 5/16", OD of 1 3/16", width of 1/2". The rod was further pushed though the center hole of the second holder (the wing nut is being rotated clockwise as the rod was pushed through). The rod end was then positioned at the other edge of the long plank (where it connected to the short plank) in order to connect to the shaft of the electric motor through a coupler (55, bore size 5/16", OD 5/8", overall length 1", Grainger 6L013).

The electric motor for the removal of the DNA from the DNA synthesis columns was a slow rpm motor of 1 revolution per minute at full speed. When the speed controller was used, the rpm could be reduced to about 20% of full speed, i.e., 0.2 rpm according to specifications. In practice, at the lowest setting, the rpm can be reduced to about 0.1 rpm, giving a flow of about 1 mL/hour, when a 10-mL syringe is used. The rpm is also affected by changes in loads using this controller. The speed controller does not give a clean linear response. An alternative is to use a constant rpm motor (0.5 rpm) of the same type with different threaded rods. With a 0.5 rpm motor using a rod of 18 threads/inch, the crossbar moves 42 mm (1 3/4") per hour. Such a rate corresponds to a 3-mL B-D syringe delivering 2.3 mL/hour, and a 1-mL syringe delivering 0.8 mL/hour.

When using a 0.5 rpm motor and a rod of 24 threads/inch, the crossbar moves 31 mm (1 1/4") per hour. This rate corresponds to a 3-mL syringe delivering 1.7 mL/hour, and a 1-mL syringe delivering 0.55 mL/hour. Thus, using different size syringes with a constant speed motor, a variation of flow rates can be obtained. In a configuration where a stepper motor-control configuration is used, a more linear response will be achieved. The timer (51) used in this configuration can be set for 1 hour; upon completion of the time, the timer turns off the motor.

The electric motor was a subfractional AC gearmotor Dayton of 1 rpm, torque in lbs start 50, run 50, overhung load 3.5 lbs, amps 0.32, input hp 1/250, Grainger 3M095. The motor used for the cartridge purification was of the same type but with an output of 18 rpm (Grainger 3M099). The speed control unit (52) (Dayton, max amps 5) permitted dial control of speeds from 20–100% of full speed on gearmotors that are driven by AC-DC (Universal) brush type motors. Dial control regulates speed; full speed was obtained by rotating dial to the extreme clockwise position. 115V, 60 Hz input. Mount in panels or directly into standard "handy" boxes. The 5 amp model uses single gang wall plate (Grainger 4X796).

The timer (51) was a spring-wound mechanical timer with a 60-minute timer range. The timer used no energy to operate, the time switch was open in "off" position (Grainger 6X546).

The mounting of all the above electrical components were done in an aluminum box (54) 6" long, 5" wide, 4" high (Byddy Industries, CU-2107-B minibox). The box was mounted on the short plank (64), with the small side towards the rod. Five holes are drilled; a 1/2" hole for the motorshaft, and four 3/16" holes, in a square, for the mounting of the motor with 4 machine screws 1/2" long. Holes were also drilled for the timer and speed control, 1/2" for the knobs, and 3/32" for fastener screws. In the side of the box was drilled a hole for the grounded cord (53, Grainger 2W685, 8 ft) to be fitted into a clamp type connector for non-metallic cable of 5/8" diameter (Gampak Products No 45650). The aluminum box was mounted with 4 metal screws to the small plank as indicated above and in FIG. 2.

The motor was set in and fastened to the box wall with 4 machine screws such that the shaft was centered to the rod on the long plank. The coupler (55) was put on the end of the rod before the motor was fastened. Once the motor was fastened, the lock screws on the coupler were tightened, one on the motorshaft and one the rod. The timer and speed control were mounted on the lid next to each other. The end of the electric cord was inserted into the box at a length of about 5". The clamp was tightened and the ground wire was mounted to the box wall. The black wire from the cord (common) was connected to a wire from the timer with wire connector (Ideal catalogue no. 30-072, model 72B). The remaining wire from the timer was connected with wire connector to one of the wires of the speed control and the remaining wire was connected to the motor. The remaining wire from the cord (white) was connected to the motor.

This was a serial connection of the common cord through timer, speed control and motor. The lid was placed on the box and fastened by mounting screws. The construction of the apparatus was thereby completed. The apparatus could be can be mounted on a stand in near vertical position or a wail in vertical position using the holes (69), cut out for this purpose.

A syringe-column-syringe assembly (66-68-67) was placed on the fiat surface of the long plank as shown in FIG. 2. The crossbar was slid down to the filled delivery syringe (66) followed by tightening of the wing nut (58) against the crossbar (65) and securing the wing nut with a nail or roll pin. The speed is set by the speed control (52) and the timer (51) is set for the length of operation. The apparatus is turned on by moving the knob of the timer to the desired time.

When the apparatus was used for the deprotection of the DNA following the removal and recovery from the DNA synthesis column, some minor modifications were made to FIG. 1, as described below. (The DNA is generally deprotected in laboratories by heating the DNA in ammonia in a sealed tube for about 5 hour at 55° C.)

The syringe-column-syringe assembly should in most cases be tightly fitted to withstand the pressure created from the ammonia being heated to 55° C. The ammonia solution was retained, without a loss of volume, upon prolonged heating of a syringe-column-syringe assembly at 55° C. for 24 hours. This has been demonstrated by the following experiment. Disposable 10-mL syringes (VWR Scientific BD 1604) and two DNA synthesis columns (Prime Synthesis, 0.2 and 1.0 micromolar) were used. The delivery syringe was filled with 2 mL of concentrated ammonia and 3 mL of air. The purpose of adding 3 mL of air to the syringe is to allow for expansion room when the assembly is heated to 55° C., similarly to the regular deprotection protocol of DNA in a sealed vial. The syringe was then connected to the column on one end, followed by connection of the receiving syringe to the other end, as already described for a syringe-column-syringe assembly. The ammonia was delivered through the system at a rate of 2.5 mL/hour. When the ammonia has been delivered, the plunger will rest at approximately 2" from the holder at the bottom of the apparatus (6 lb).

A thermocouple (Grainger 6A843) is mounted on the unit through the crossbar and one holder (61a) and connected to a temperature controller (Grainger 4A481) that is set at 55° C. and connected to a heat lamp. After the ammonia has been delivered (the 1-hour removal), a heat lamp (Grainger 2V653 mounted on a stand with box 2V654 and cover 2V655, with Philips Infrared Lamp 250 watts), positioned in front of the unit, which is in the preferred upright position, at a distance of 6", is turned on by a regular 24-hour household timer. When the temperature reaches 55° C., the lamp is turned off. When the temperature has fallen about 2 degrees, the controller turns on the lamp until the set temperature is reached. The household timer is set for 10 hours, when the deprotection is completed. When the unit has cooled off, the DNA can be used for other applications.

In order to control the amount of expansion (when this assembly is heated to 55° C., the plunger of the receiving syringe is capable of moving entirely to the holder 61b), a spacer made of mahogany 1"×1"×2" (71) is put on the bottom of the unit against the holder (61) for each assembly unit in order prevent the plunger from moving all the way to the holder. Two additional holes are drilled for roll pins, and the pins positioned in front of the sleeve of the receiving syringe (70), the same way it is mounted at the delivery syringe; this is added for each assembly unit. If that is not done, the pressure generated inside will eventually push the syringe off the plunger when the plunger reaches the holder. The unit can be exposed as shown, but it is preferred to cover the unit with an aluminum lid to improve heat distribution and safety in case the assembly accidentally explodes under the pressure due to human error or faulty columns or syringes.

The heating of the ammonia above room temperature can be achieved with a number of other heating devices. Some are listed below with reference to VWR Scientific stock numbers: block heaters (13259-005), heat gun (26404-865), infrared heat (33872-003, 33810-006), heating tapes (33735-104), and immersion heaters (33899-082). The last item may be preferred when the apparatus is made of metal since the heat loss will be greater for such a unit compared with a wood or plastic construction.

Cartridge purification can be performed using the unit with the above described configuration. It may be desirable to change the rpm of the motor to a higher rpm, as has been indicated, since higher flow rates are used in cartridge purification. A preferred configuration for cartridge purification would include a faster rpm motor and a timer with a shorter time range, i.e. 5 minutes instead of 60 minutes or more. A 5-minute range timer which fit into this configuration is Grainger 6X545.

Alternatively, the cartridge purification and DNA removal/recovery system disclosed here may not have a timer at all. Instead the unit could be equipped with limit switches which turn off the motor when the delivering syringe has been emptied. The sensor of the limit switch should be positioned on the apparatus such that it is activated when the delivering syringe has been emptied or near emptied. Examples of such switches are listed with the Grainger catalog number: enclosed snap-action switches (Grainger 3A096), limit switches (Grainger 3A094), proximity switches (Grainger 2A188), capacity switches (Grainger 4A331), photoelectric switches (Grainger 4A335).

EXAMPLE 2

Use in Resin DNA Cleavage and DNA Recovery

DNA synthesized on a 0.2 micromolar scale using adenosine (A), thymidine (T), guanosine (G), cytidine (C) or a modified nucleoside attached to the support through an ester bond at the 3'-position of the deoxyribonucleotide ranging from 1- to about 250-nucleotides long, depending on the capacity of the DNA synthesizer that is used, is removed as follows.

Concentrated aqueous ammonia (5 mL) is filled in the delivering syringe (66) and attached to the column (68) using a luer fitting. Similarly, an empty syringe (67) is attached at the other end of the column. The syringe-column-syringe assembly is put on the flat surface of the apparatus between the pins (59). The crossbar (65) is snug fitted against the syringe plunger and the wing nut (58) is turned to fit tightly against the crossbar, without emptying the delivery syringe (a slight amount of ammonia may be released into the resin as a result of this operation). The lock pin is put in to secure the wing nut.

The unit is turned on and the flow rate is set for 2 mL/60 min, by speed control (52). The timer is set for 60 minutes, at which time the apparatus unit is automatically turned off. The ammonium hydroxide is slowly passed through the column and collected in the receiving syringe fitted to the other end of the column. The ammonia solution containing the recovered DNA may be transferred to a vial for the remaining steps of the synthesis, such as deprotection of the nucleotide bases, the phosphorous, and the 5'-hydroxyl, following common DNA synthesis protocol.

The recovered amount of crude DNA synthesized from a 0.2 micromolar scale varies, but it is in the range 500 to 1500 micrograms for DNA made on a 500A pore size DNA synthesis column. When 1000A pore size is used, generally lesser amounts of DNA are obtained, this difference attributed to different chemical characteristics of the solid silica matrix.

EXAMPLE 3

Use in Synthetic DNA Deprotection

The DNA that was removed from the solid support is contained in the aqueous ammonia solution. If the DNA was recovered by the above procedure, it would be contained in the receiving syringe. The DNA can be deprotected in a vial by heating to 55° C. in a water bath, or the DNA can be deprotected by use of the apparatus for which the apparatus may be prepared for the deprotection step as follows.

The receiving syringe is secured by the additional roll pins and spacers as previously described, to control the amount of expansion upon heating the ammonia. The thermocouple is mounted and positioned parallel and adjacent to the syringe assembly. The apparatus is covered with the metal cover for even heat distribution. The heat lamp is positioned 6" away, ⅓" above the base of the apparatus. The temperature controller is set for 55° C., and the regular household timer for the control of the heat lamp is set for 5 hours or more, depending on the operator's schedule (10 hours may be convenient for an overnight run).

If the deprotection is desired to immediately follow the removal/recovery step, the above preparation should be made before the removal/recovery is started. The heat lamp timer is set to start in 1 hour (at which time the recovered DNA is residing in the receiving syringe), and set to end 5 or more hours later.

EXAMPLE 4

Use in Synthetic DNA Purification

When purification of DNA by cartridge is desired, the DNA synthesizer is programmed to complete the synthesis without removing the lipophilic dimethoxytrityl group (DMT-) from the 5'-end of the DNA; this may be referred to as trityl-on DNA (DMT-DNA). The DNA is first removed from the DNA synthesis column and then deprotected (at the bases and phosphorus) in a sealed tube at 55° C. for at least 5 hours following commonly used manual operations, or by the disclosed automated methods of removal/recovery and deprotection using the syringe assembly on the apparatus depicted in FIGS. 2 and 3.

The cartridge purification procedure described below is that recommended by Applied Biosystems for the "Oligonucleotide Purification Cartridges 400771 (OPC™ cartridge)-patent pending". This procedure may be adapted, fully or in part, for use in the disclosed device. As recommended by Applied Biosystems:

Solutions needed: HPLC grade acetonitrile, 5 mL (part no. 400262); 2.0 M triethylammonium acetate, 5 mL (pan no. 400613); deionized water; 1.5 M ammonium hydroxide, 15 mL (1:10 dilution of concentrated ammonium hydroxide in deionized water); 2% trifluoroacetic acid, 5 mL (1:50 dilution of neat TFA part no. 400137); 20% v/v acetonitrile in deionized water, 1 mL.

1. After completion of trityl-on synthesis, cleave the oligonucleotide from the support and deprotect following normal protocols for the synthesis method used.

2. Connect an all polypropylene syringe (Aldrich Z11686-6); an OPC™-cartridge, and male-to-male luertip. Make sure all fittings are snug. The OPC™-cartridge may be immobilized with a laboratory clamp.

3. Flush the cartridge with 5 mL of HPLC grade acetonitrile, followed by 5 mL of 2.0 M triethylammonium acetate. Remove the syringe from the cartridge before removing the plunger; then re-insert the syringe barrel prior to the next addition.

4. Dilute an aliquot containing about 20 OD units of the crude, deprotected oligonucleotide still in concentrated ammonia with one third volume of deionized water. The final volume of the solution should be 1 to 4 mL.

IMPORTANT: Keep the flow rate at 1 to 2 drops per second for all subsequent reagent additions.

5. Place this solution (step 4) in the syringe and slowly push it through the cartridge. Save the eluted fraction, place it in the syringe, and gently push it through the cartridge. Again, this will load 1 to 5 OD units of the crude oligonucleotide (depending on length, sequence and synthesis quality) onto the cartridge.

6. Slowly wash the cartridge with 3×5 mL of 1.5 M ammonium hydroxide.

7. Flush the cartridge with 2×5 mL of water.

8. Detrylate the OPC™ bound oligonucleotide with 5 mL of 2% trifluoroacetic acid solution. Gently push about 1 mL through the cartridge, wait minutes, then flush the remaining TFA solution through the cartridge.

9. Flush the cartridge with 2×5 mL aleionized water. For sequences longer than 40 bases, add this step 9a.
Gently push through the cartridge 1×5 mL of 1.5 M ammonium hydroxide, followed by 2×5 mL of deionized water.

10. Elute the purified, detrylated oligonucleotide by slowly washing the cartridge with 1 mL of the 20% acetonitrile solution.

11. Determine the OD units at 260 nm with an aliquot of the eluate from step 10.

12. Store the cartridge purified oligonucleotide as a dry solid at −20° C.

(OPC™ is a trademark of Applied Biosystems, Inc. Applied Biosystems, 850 Lincoln Center Dr., Foster City, Calif. 94404.)

The automation of DNA removal from DNA synthesis columns would increase the efficiency of laboratory personnel, freeing time for other laboratory work and freeing up those DNA synthesizers (that are equipped with the cleavage feature) for DNA synthesis. The removal of DNA from DNA synthesis columns can be performed by automation, with up to 4 different samples for this specifically disclosed apparatus. The number of samples that may be processed simultaneously is not limited to 4 because several apparatus can be used or a modification of the apparatus configuration to accept more than 4 syringe-assemblies can easily be done.

The use of the removal/recovery features of this apparatus in combination with the deprotection protocol is unique. It has been a long sought feature for the DNA synthesis laboratories since it would carry the currently available automation to a higher level. With currently available procedures, the researchers time is restricted by the ability to perform one DNA cleavage reaction at a time. If the cleavage feature is utilized on the DNA synthesizer, the DNA synthesizer is fled up and unavailable for synthesis. This apparatus allows the DNA synthesis column to be transferred to the apparatus for removal/recovery, followed by the deprotection step (the deprotection may also be done as a separate operation). By having this new apparatus in a laboratory, the researcher eliminates the need for the much more expensive DNA synthesizers with the automatic cleavage features.

When this apparatus is applied to DNA cartridge purifications, the efficiency and reproducibility of the operation is increased compared with the manual methods available. The steps involved in the purification have been described above. The procedure requires several different steps for introducing reagent, solvents and washing procedures.

When this apparatus is used in the purification applications, it will be used in the semi-automated mode. For each step, the delivering syringe has to be loaded with the appropriate chemical and/or solvent for that particular step, and the content in the receiving syringe has to be disposed of, or recovered, depending on the particular step in the purification procedure. The cartridge purification protocols provided by cartridge manufacturers are entirely manual processes where chemicals and solvents are delivered to the cartridge in a prescribed order.

Using the disclosed configuration of this apparatus, 4 purifications on cartridges can be performed at the same time with identical delivery times and reaction times of the reagents for all 4 cartridges. Without this device a researcher has to go through each step separately, and to repeat it 4 times, to achieve the same result that this apparatus can achieve in one operation for each individual step. Additionally, some cartridges are packed so tightly that it becomes a physical burden to push the syringe contents through the cartridge at the amounts and rates prescribed by the manufacturers. It is, therefore, tempting for the users to take some shortcuts to reduce the prescribed delivery amount. The use of this apparatus eliminates that physical burden and potential temptation for shortcuts.

EXAMPLE 5

Basic/Acidic) Precipitating Solvent Reagents for Use in Non-ammonia Processing

The following procedure was employed as an alternative to the use of ammonia in the cleavage and deprotection of newly synthesized DNA, using the apparatus of the present invention.

Specifically, Reagent A was prepared as aqueous sodium hydroxide at 0.5 Molar concentration (2 g in 100 mL). A concentration range of 0.1–2.0 Molar was anticipated to be acceptable in the protocol. The 15-minute cleavage time from the column was considered optimal, although 5 to 10 minutes may be sufficient. At higher concentrations of the reagent, the cleavage will occur more rapidly.

A deprotection time of 30 minutes at 85° C. was assumed fairly optimal, although a shorter time, e.g., on the order of about 10 to about 15 minutes will be sufficient. Using higher concentrations of sodium hydroxide, the deprotection time can be shortened. At a temperature of about 55° C., the deprotection was complete within 24 hours. The optimal times for such purposes was determined by comparing the product profiles on capillary electrophoresis with samples obtained from the regular ammonia deprotection protocol at 55° C., using model sequences of DNA, 20 nucleotides long.

When the optimized conditions had been determined by capillary electrophoresis, i.e., products the automated protocol of the present invention look the same as products derived from the well established ammonia deprotection protocol, the DNA was further analyzed by snake venom digestion.

The DNA was cleaved into monomers using snake venom phosphodiesterase and then treated with alkaline phosphatase to form four nucleosides in the sequence. The mixture was analyzed by HPLC (high performance liquid chromatography). The composition of nucleosides in samples using the non-ammonia based protocol was indistinguishable from the composition of the same sequence protected using an ammonia deprotection protocol such as described above. Finally, the DNA prepared using the on-ammonia based protocol has been used in several molecular biology experiment, as sequencing primers, PCR primers, probes, primer extension, etc, and appears to perform as well as that prepared using the protocol involving ammonia.

The precipitation of synthesized DNA using the present non-ammonia reagents seemed to work particularly well, perhaps because the sodium salt of DNA is less soluble in organic solvents, as compared to the ammonium salt obtained when ammonia is used in the deprotection protocol.

The Reagent B (precipitation and neutralizer) was prepared as 3 g of concentrated acetic acid in 500 mL 2-propanol. By using 5 volumes of that solution to 1 volume of cleavage/deprotection reagent A, the mixture was neutralized to sodium acetate and the excess solvent precipitated the DNA. The sodium acetate at that concentration did not appear to precipitate measurably with the DNA.

When the lipophilic DMT (dimethoxytrityl) group was kept on the DNA for further affinity chromatography (purification) of the DNA, Reagent C (neat 2-propanol) was used instead of Reagent B. The acetic acid was omitted since the DMT-group is acid labile.

After the completion of DNA synthesis, the following processing protocol allowed for the DNA to be ready for molecular biology experiments in about 1 hour. This is a dramatic improvement in processing time, in fact it is an order of magnitude faster than traditional protocols using ammonia. The use of this protocol on the apparatus of the present invention makes the entire synthetic operation automatic and more efficient.

EXAMPLE 6

Cleavage, Deprotection, and Recovery of Fully Deprotected Synthetic DNA

Materials:

Reagent A (GREEN): cleavage and deprotection solution.

Reagent B (RED): precipitation and neutralizing solution.

The reagents are prepared as described in Example 5 above, and are stored at room temperature. The reagents should only be used in accordance with accepted safety practices and precautions, including in a vented area, wearing personal protective equipment, and avoiding use near open flames or high temperatures.

Procedure for Fully Deprotected DNA at 0.2 micromolar scale (For a 1.0 micromolar DNA synthesis, use 1 mL of Reagent A (GREEN). Divide the product mixture into four centrifuge tubes of 0.25 mL samples each. For a 30–50 nmol synthesis, follow the procedure for a 0.2 micromolar (200 nmol) DNA synthesis.)

1. Fill a 3-mL syringe (plastic type with a luer slip tip) with 0.5 mL of Reagent A (GREEN), follow by pulling up 0.5 mL of air. The volume of air will ensure that the void volume in the column is completely emptied during the cleavage step.

Connect the syringe to the synthesis column and connect an empty syringe at the other end of the column. Gently push the plungers on the syringes before starting the procedure to make sure that they will move smoothly.

Feed in about 0.2 mL of reagent and let stand for 5 minutes. Then, feed another 0.2 mL of reagent and let stand 10 minutes. Finally, feed in the remaining 0.1 mL including the air bubble to ensure the void volume is emptied.

When the cleavage is complete, transfer the product mixture in the receiving syringe to a 1.5-mL microcentrifuge tube (Eppendorf®-type (Eppendorf-Netheler-Hinz GmbH)) and incubate in an oven or water bath at 85° C. for 30 minutes. Allow the reaction tube to cool (about 5 minutes).

2. Transfer half of the reaction mixture into a second centrifuge tube.

Add 5 volumes (1.25 mL, or as much as the centrifuge will hold) of Reagent B (RED). Vortex for 30–60 seconds. At this point, the mixture will usually become slightly cloudy. Let stand for 10–20 minutes in a freezer.

3. Centrifuge at 15,000 rpm for 10 minutes. Even sequences as short as 15 nucleotides long will precipitate readily.

4. After the centrifugation, decant the solution and allow the tube dry for a few seconds upside down. Dry the pellet in a low oven (< 50° C.) or in a Speedvac® instrument (Savant Instruments, Inc.) under vacuum; this will turn the glass-like pellet into a white pellet. The DNA is now ready for quantification and use in molecular biology applications.

(If however, there is no immediate need for the DNA, the following simple procedure will turn the pellet into a flocculent precipitation—like a cottonball of DNA. Wash the pellet with 70% aqueous ethanol (3×0.03 mL), making sure the pellet does not come loose (otherwise, centrifuge again). Let the centrifuge tube rest upside down for a few seconds to dry the pellet. Next, take up the pellet in 50–100 μL of water, and dissolve by heating in a water bath for 5 minutes at 35°–50° C. Centrifuge, and cool to room temperature, concentrate at reduced pressure for 1–2 hours in a Speedvac®. The resultant product will look like a nice cotton ball of DNA.

EXAMPLE 7

Protocol for Rapid Cleavage, Deprotection, and Recovery of DMT-DNA

Materials:

Reagent A (GREEN): cleavage and deprotection solution.

Reagent C (YELLOW): precipitation solution for DMT-DNA.

The reagents are prepared as described in Example 5 above, and are stored at room temperature. The reagents should only be used in accordance with accepted safety practices and precautions, including in a vented area, wearing personal protective equipment, and avoiding use near open flames or high temperatures.

Procedure for DMT-DNA at 0.2 micromolar scale For a 1.0 micromolar DNA synthesis, use 1 mL of Reagent A (GREEN). Divide the product mixture into four centrifuge tubes of 0.25 mL samples each. For a 30–50 nmol synthesis, follow the procedure for a 0.2 micromolar (200 nmol) DNA synthesis.

1. Fill a 3-mL syringe (plastic type with a luer slip tip) with 0.5 mL of Reagent A (GREEN), follow by pulling up 0.5 mL of air (to ensure that the void volume in the column is completely emptied during the cleavage step).

Connect the syringe to the synthesis column and connect an empty syringe at the other end of the column. Gently push the plungers on the syringes before starting the procedure to make sure that they will move smoothly.

Feed in about 0.2 mL of reagent and let stand for 5 minutes. Then, feed another 0.2 mL of reagent and let stand 10 minutes. Finally, feed in the remaining 0.1 mL including the air bubble to ensure the void volume is emptied.

When the cleavage is complete, transfer the product mixture in the receiving syringe to a 1.5-mL microcentrifuge tube (Eppendorf®-type) and incubate in an oven or water bath at 85° C. for 30 minutes. Allow the reaction tube to cool (about 5 minutes).

2. Transfer half of the reaction mixture into a second centrifuge tube.

Add 5 volumes (1.25 mL, or as much as the centrifuge will hold) of Reagent C (YELLOW). Vortex for 30–60 seconds. At this point, the mixture will usually become slightly cloudy. Let stand for 10–20 minutes in a freezer.

3. Centrifuge at 15,000 rpm for 10 minutes. Even sequences as short as 15 nucleotides long will precipitate readily.

4. After the centrifugation, decant the solution and allow the tube dry for a few seconds upside down.
Wash the pellet with 70% aqueous ethanol (3×0.03 mL), making sure the pellet does not come loose (otherwise, centrifuge again). Let the centrifuge tube rest upside down for a few seconds to dry the pellet. The DNA is now ready for cartridge or HPLC purification.

5. Take the pellet up in 0.1 M triethylammonium acetate, isolate by HPLC. Alternatively, the pellet may be taken up in 10% aqueous ammonia (or preferentially, 0.1 M triethylammonium acetate) and isolate by cartridge purification.

EXAMPLE 8

Automated Cleavage and Deprotection of Synthetic DNA

The following procedure is useful for the cleavage and deprotection of DNA by use of the above-described Reagents (deprotection at 85° C.). It is applicable for DNA synthesis columns presently commercialized by Beckman Instruments (Oligo 1000 DNA Synthesizer).

1. Connect the 12 volt power supply on top of the unit. Then, connect the 120 VAC wall plug.

2. Set the total time of the operation to 60 minutes (20 minutes cleavage + 40 minutes deprotection) on the electronic time (red). Turn the (+/−) knob clockwise to the desired time. Upon completion of the operation, the time beeps 6 times and the window becomes dark.

The set time is stored in the memory. For the next operation, push the (on/off) button once, and the time window will show the present time of 60 minutes. If a new time is used, set the timer with the (+/−) knob.

3. Set the cleavage time on the time relay (grey) by turning the knob to 2. The scale is set at 0–60 minutes; i.e., 1= 10 min, 2= 20 min, 3= 30 rain, 6= 60 min.

4. Pre-set adjustments have been made for 3-mL "B-D" syringes (plastic disposable syringes with luer slip tips).

5. For 0.2 micromolar synthesis: Fill the syringe with 0.5 mL of Reagent A (green), followed by pulling up 0.5 mL of air. The volume of air will ensure that the void volume in the column is completely emptied during the cleavage step. Tightly connect the syringe to the Beckman column-vial assembly, and put the assembly on the machine, with the syringe in the holder and the vial in the heating block.

For 30 or 50 Nmol synthesis: Follow the procedure for 0.2 micromolar synthesis.

For 1 micromolar synthesis: Use 1.0 mL of Reagent A.

6. Adjust the cross-bar against the syringe plunger and gently tighten the cross-bar handle (not too hard). Fasten the splash guard on the unit.

7. Start the operation by pushing the (on/off) button once.

8. During the cleavage operation, the relay is blinking a red light. When the relay switches to the heating mode after the cleavage is completed, two solid red lights are shown. When the total time has elapsed (the remaining time is seen at the timer window), the timer turns the unit off, and the window becomes dark.

9. Allow the heating block to cool 10 minutes before removing the syringe-column-vial assembly from the machine. Allow the vial to cool to room temperature before precipitation of the DNA.

10. Continue with step #2 in the protocol for the precipitation and recovery of the DNA.

EXAMPLE 9

Improved Cleavage and Deprotection

The apparatus described and used in Example 3 was further improved in order to provide a cleavage and deprotection system by use of concentrated ammonia at 55° C., according to the following protocol:

1. Set the flow rate for the cleavage operation (see the flow rate chart for 12 volt and 3–9 volt power supply in cleavage unit instructions). Connect the power supply on top of the unit. Reminder: When putting on or removing the DC power supply on the unit, always have the 120 VAC cord disconnected from the wall outlet.

2. Set the total time of the operation (cleavage + deprotection time) on the electronic timer (red). Turn the (+/–) knob clockwise to the desired time. Upon completion of the operation, the timer beeps 6 times and the window becomes dark.

The set time is stored in the memory. If the same time is used for the next operation, push the (on/off) button once, and the timer window will show the previous setting. If a new time is used, set the timer with the (+/–) knob.

3. Set the cleavage time on the time relay (grey) by turning the knob. The scale is set at 0–180 minutes; i.e., 6= 60 rain, 9= 90 rain, 12–120 rain, 18= 180 min. The time relay has a range of 1 second to 180 hours.

4. Preset adjustments have been made for 3-mL B-D syringes. If other syringes are used, follow simple adjustment procedures can be used for the upper syringe holders. The syringe holders can be adjusted in the following manner as to ensure that the cross bar will stop moving when the syringe is empty. Two syringes should be placed in the middle positions of the upper holder. The retaining screws of the upper syringe holder should be loosened and the holder slid down to allow it to slide to its lowest position. Move the cross bar against the plungers of the syringes and tighten the cross bar in position. Push the syringe holder up until it stops when the cross bar reaches the threads. Tighten the screws on the syringe holder. This procedure will ensure that there are no threads available to drive the cross bar further down when the syringe is empty. This procedure, as well as the flow rates themselves, can be set at the time of manufacture for standard delivery syringes, or can be adjusted by the user.

5. Fill the syringe with ammonia and connect to the synthesis column. Connect the male-male luer connector to the other end of the column, followed by a 1.5-inch needle. It is recommended that the needle be put on last to minimize the potential for any accidental hazards.

6. Put a 4-mL vial, equipped with a screw cap and septa, in the heating block. Push the needle through the septa near the center. Lastly, insert the syringe into the syringe holder (keeping the entire syringe-column-needle assembly in as upright a position as possible to minimize the tension in the septa).

7. Adjust the cross-bar against the syringe plunger and tighten the cross-bar handle (not too hard). Fasten the splash guard on the unit.

8. Start the operation by pushing the (on/off) button once.

9. During the cleavage operation, the relay is blinking a red light. When the relay switches to the heating mode after the cleavage is completed, two solid red lights are shown. When the total time has elapsed (the remaining time is seen at the timer window), the timer turns the unit off, and the window becomes dark.

10. Allow the heating block to cool to room temperature before removing the syringe-column-needle assembly from the machine.

| Flow Rates for 12 volt and 3–9 volt power supplies with 3-mL syringes | |
| --- | --- |
| 12.0 volt | 3.0 mL/h |
| 9.0 volt | 2.2 mL/h |
| 7.5 volt | 1.9 mL/h |
| 6.0 volt | 1.5 mL/h |
| 4.5 volt | 1.1 mL/h |
| 3.0 volt | 0.8 mL/h |

While only certain embodiments of the present invention have been described in specific details, it will be apparent to those skilled in the art, that many other specific embodiments may be practiced and many changes made, all within the spirit of the invention and the scope of the appended claims:

What is claimed is:

1. An apparatus for the automated delivery of a liquid through a substantially cylindrical column containing solid matrix, the apparatus comprising,
   (a) a substantially cylindrical column, comprising a solid matrix, said column having, at opposite ends thereof, an inlet port and an outlet port, said inlet port being in fluid communication with said delivery means,
   (b) syringe-like liquid delivery means comprising a movable plunger within a cylindrical barrel, said delivery means being capable of receiving and holding said liquid and being in fluid communication with said inlet port of said column, and capable of delivering said liquid into said inlet port of said column upon depression of said plunger,
   (c) liquid receiving means in fluid communication with said outlet port of said column,
   (d) drive means capable of depressing said plunger in a controlled fashion, comprising;
      (i) plunger engagement means for contacting, in order to depress, said plunger,
      (ii) linkage means capable of moving said plunger engagement means in response to the operation of a motor, and
      (iii) a motor capable of moving said engagement means at a controlled rate to depress the plunger, thereby delivering said liquid to said column, and
   (e) support means capable of retaining said drive means in operational alignment with said delivery means, and capable of releasably receiving and supporting said barrel, said column, and said receiving means in axial alignment with each other.

2. An apparatus according to claim 1 wherein said apparatus is capable of simultaneously retaining, and delivering liquids through, a plurality of parallel columns, the apparatus comprising,
   (a) a plurality of parallel and substantially cylindrical columns, each comprising a solid matrix, each of said columns having, at opposite ends thereof, an inlet port and an outlet port, said inlet port being in fluid communication with said delivery means,
   (b) a plurality of syringe-like liquid delivery means, each comprising a movable plunger within a cylindrical barrel, said delivery means being capable of receiving and holding said liquid and being capable of delivering said liquid into said inlet port of its respective column upon depression of said plunger,
   (c) liquid receiving means in fluid communication with said outlet ports of said columns,
   (d) drive means capable of simultaneously depressing said plungers in a controlled fashion, comprising;

(i) plunger engagement means for contacting, in order to depress, said plungers, (ii) linkage means capable of moving said plunger engagement means in response to the operation of a motor, and (iii) a motor capable of moving said engagement means at a controlled rate to depress said plungers, thereby delivering said liquids to said columns, and (e) support means capable of retaining said drive means in operational alignment with said delivery means, and capable of releasably receiving and supporting respective barrels, said columns, and said receiving means in axial alignment with each other.

3. An apparatus according to claim 2 wherein said receiving means comprises a substantially solid block having a plurality of liquid passageways therein, each of said passageways:

(a) being substantially parallel to each other (b) being substantially parallel to, and in axial alignment with, a respective column, (c) being in liquid communication with said outlet port of said respective column, and (d) channeling into a common outlet channel running substantially perpendicular to the direction of the passageways.

4. An apparatus according to claim 2 wherein said receiving means comprises a plurality of syringes, each being retained in liquid communication with the outlet port of its respective column.

5. An apparatus according to claim 1 wherein said receiving means comprises a heated block containing a plurality of collection vials, each of said vials being in axial alignment and fluid communication with the outlet port of a respective column.

6. An apparatus according to claim 1 further comprising means for controllably heating associated with said columns and capable of heating said columns to a temperature above ambient temperature.

7. An apparatus according to claim 1 wherein said solid matrix is a polymeric support and said column further comprises a biopolymer covalently attached to said solid matrix.

8. An apparatus according to claim 7 wherein said biopolymer is DNA containing a lipophilic protecting group at the 5'-end of the DNA sequence.

9. A process for the removal, recovery, deprotection, and/or purification of biopolymers from a solid matrix, the process comprising the steps of:

(a) providing a substantially cylindrical column, comprising a biopolymer attached to a solid matrix, said column having, at opposite ends thereof, an inlet port and an outlet port, said inlet port being in fluid communication with said delivery means, (b) providing an apparatus comprising (i) syringe-like liquid delivery means comprising a movable plunger within a cylindrical barrel, said delivery means being capable of receiving and holding said liquid and being capable of delivering said liquid into said inlet port of said column upon depression of said plunger, (ii) liquid receiving means in fluid communication with said outlet port of said column, (iii) drive means capable of depressing said plunger in a controlled fashion, comprising;

a. plunger engagement means for contacting, in order to depress, said plunger, b. linkage means capable of moving said plunger engagement means in response to the operation of a motor, and c. a motor capable of moving said engagement means at a controlled rate to depress the plunger, thereby delivering said liquid to said column, and (iv) support means capable of retaining said drive means in operational alignment with said delivery means, and capable of releasably receiving and supporting said barrel, said column, and said receiving means in axial alignment with each other, (c) attaching said column to said apparatus in order to provide fluid communication between said delivery means and said inlet port of said column, and between said receiving means and said outlet port of said column, (d) sequentially delivering desired liquids useful for the removal, recovery, deprotection, and/or purification of said biopolymer through said column from said delivery means, and (d) recovering desired fractions of said delivered liquids in said receiving means.

10. A process according to claim 9 wherein said sequential delivery of desired liquids comprises the sequential delivery of a basic solution for the cleavage and deprotection of DNA, followed by an acidic precipitating solvent for the precipitation and neutralization of the DNA.

11. A process according to claim 10 wherein the basic solution is a solution of 0.1 molar to 2 molar sodium hydroxide and said acidic precipitating solvent reagent is a solution of acetic acid in 2-propanol.

12. A process according to claim 9 wherein said sequential delivery of desired liquids comprises the sequential delivery of a basic solution for the cleavage and deprotection of DNA, followed by a solvent solution for the precipitation of DMT-DNA.

13. A process according to claim 12 wherein the basic solution is a solution of 0.1 molar to 2 molar sodium hydroxide and said solvent solution is 2-propanol.

* * * * *

UNITED STATES PATENT AND TRADEMARK OFFICE
CERTIFICATE OF CORRECTION

PATENT NO. : 5,496,473
DATED : March 5, 1996
INVENTOR(S) : Flora Chow

It is certified that error appears in the above-indentified patent and that said Letters Patent is hereby corrected as shown below:

Column 22, line 29, replace "3= 30 rain" with --3= 30 min.--.

Column 23, line 21, replace "6= 60 rain, 9= 90 rain, 12- 120 rain" with -- 6= 60 min., 9= 90 min., 12- 120 min.--.

Signed and Sealed this

Sixteenth Day of July, 1996

Attest:

BRUCE LEHMAN

Attesting Officer     Commissioner of Patents and Trademarks